US008109270B2

(12) United States Patent
Hoffmann

(10) Patent No.: US 8,109,270 B2
(45) Date of Patent: Feb. 7, 2012

(54) DISPENSING VALVE FOR BREATHING GAS

(75) Inventor: Karsten Hoffmann, Kasseedorf/Griebel (DE)

(73) Assignee: Dräger Medical GmbH, Lübeck (DE)

(*) Notice: Subject to any disclaimer, the term of this patent is extended or adjusted under 35 U.S.C. 154(b) by 1022 days.

(21) Appl. No.: 12/034,817

(22) Filed: Feb. 21, 2008

(65) Prior Publication Data

US 2008/0223368 A1 Sep. 18, 2008

(30) Foreign Application Priority Data

Mar. 16, 2007 (DE) ......................... 10 2007 012 729

(51) Int. Cl.
*A62B 9/02* (2006.01)
*A62B 9/00* (2006.01)

(52) U.S. Cl. .............................. 128/205.24; 128/200.24

(58) Field of Classification Search ............. 128/200.24, 128/205.24; 137/528, 495, 505.14, 505.42, 137/906, 505.12, 505.11, 544; 251/52, 54, 251/95, 121.1

See application file for complete search history.

(56) References Cited

U.S. PATENT DOCUMENTS 3,752,175 A * 8/1973 Hamilton et al. ............ 137/81.1
3,795,257 A * 3/1974 Fabish et al. .................. 137/491
5,016,627 A * 5/1991 Dahrendorf et al. ..... 128/205.24
5,165,398 A * 11/1992 Bird ......................... 128/204.25
5,464,009 A * 11/1995 Tatarek-Gintowt ...... 128/205.24
6,155,290 A * 12/2000 Nakajima et al. ........ 137/505.41
6,176,256 B1 * 1/2001 Nakajima et al. ........ 137/505.12
7,331,345 B2 * 2/2008 Haston ..................... 128/204.29
2005/0056319 A1 * 3/2005 Hasegawa et al. ....... 137/505.42

FOREIGN PATENT DOCUMENTS

DE 28 27 131 C2 12/1981
DE 40 12 485 C1 12/1990

* cited by examiner

*Primary Examiner* — Annette Dixon

(74) *Attorney, Agent, or Firm* — McGlew and Tuttle, P.C.

(57) ABSTRACT

A dispensing valve with admission pressure compensation and a safety device for maximum pressure limitation of the admission pressure. To accomplish the object, a deformation zone (18), which can be brought into contact with a support surface (14) by the admission pressure by admitting pressure in the direction of a reduction of the active area of the compensating diaphragm (10), is provided in the area of a compensating diaphragm (10).

11 Claims, 2 Drawing Sheets

DISPENSING VALVE FOR BREATHING GAS

CROSS REFERENCE TO RELATED APPLICATIONS

This application claims the benefit of priority under 35 U.S.C. §119 of German Patent Application 10 2007 012 729.6 filed Mar. 16, 2007, the entire contents of which are incorporated herein by reference.

FIELD OF THE INVENTION

The present invention pertains to a breathing gas dispensing valve with admission pressure compensation and a safety means for limiting maximum admission pressure.

BACKGROUND OF THE INVENTION

A dispensing valve for breathing gas is known from DE 28 27 131 C2. The regulating member for dispensing the gas is formed by a ball valve with a gas passage opening, and a ball is pressed by the admission pressure against the gas passage opening. The ball can be pushed out of the gas passage opening with a pin, which can be displaced in the longitudinal direction. The pin is actuated by a magnetic drive. The gas flow through the gas passage opening results from the path by which the ball is displaced in relation to the gas passage opening and the pressure difference between the two sides of the gas passage opening.

The area of the dispensing valve in which the admission pressure acts must always be designed for the maximum possible pressure in the case of the first error. This requires increased technical effort and special permits may possibly be necessary for certain gases.

Admission pressure compensation is frequently employed to make it possible to actuate dispensing valves with weak opening forces at high admission pressures. A dispensing valve with admission pressure compensation is described, for example, in DE 40 12 485 C1. A compensating piston with a pot-shaped diaphragm, which diaphragm is accommodated in a valve housing, is provided for admission pressure compensation. The admission pressure compensation takes place in such a way that a compensating force, which is generated at the pot-shaped diaphragm and the compensating piston, counteracts the force acting on the valve body. A safety means for liming the admission pressure is not provided. Such a safety means could be embodied with a separate pressure relief valve only.

SUMMARY OF THE INVENTION

The basic object of the present invention is to propose a dispensing valve with admission pressure compensation and with a safety means for the maximum pressure limitation of the admission pressure.

According to one aspect of the invention, a dispensing valve with admission pressure compensation is provided. The dispensing valve comprises an admission pressure chamber, a back pressure chamber, a valve drive, a working diaphragm between the admission pressure chamber and the back pressure chamber, a compensation chamber connected to the admission pressure chamber, an expansion chamber, a compensating diaphragm between the compensation chamber and the expansion chamber, a push rod and a deformation zone within the compensating diaphragm. The expansion chamber has a support surface extending at a spaced location from the compensating diaphragm. The push rod is actuated by the valve drive and connects the working diaphragm to the compensating diaphragm. The deformation zone is provided within the compensating diaphragm. The deformation zone is brought into contact with the support surface by admission pressure in the compensation chamber providing a reduction of an active area of the compensating diaphragm.

The compensating diaphragm may consist of a solid middle part connected to the push rod and a flexible outer part that is deformable by admitting pressure. The outer part may have a circumferential bead as a deformation zone.

According to another aspect of the invention, a breathing dispensing valve with admission pressure compensation is provided. The dispensing valve comprises an admission pressure chamber with an inlet connected to a pressurized gas source, a back pressure chamber with a breathing gas outlet leading to a user and with a valve seat, a valve drive, a working diaphragm connected to the valve drive and disposed between the admission pressure chamber and the back pressure chamber, a compensation chamber connected to the admission pressure chamber, an expansion chamber having an expansion chamber pressure, a compensating diaphragm, a push rod and a deformation zone defined by the compensating diaphragm. The working diaphragm closes a connection between the admission pressure chamber and the back pressure chamber in a seated position on the valve seat, the valve drive driving the working diaphragm from the seated position into an open position opening the connection between the admission pressure chamber. The compensating diaphragm is disposed between the compensation chamber and the expansion chamber and is acted on, on a compensation chamber side by admission pressure and is acted on, on an expansion chamber side by expansion chamber pressure. The expansion chamber has a support surface extending at a spaced location from the compensating diaphragm. The push rod is connected to the valve drive and connects the working diaphragm to the compensating diaphragm. The deformation zone is defined by the compensating diaphragm. The deformation zone is brought into contact with the support surface in a deformation zone contact state, based on admission pressure and expansion chamber pressure acting on the compensating diaphragm. The compensating diaphragm has a reduced surface exposed to admission pressure in the deformation zone contact state, liming the compensating force acting on the working diaphragm due to a reduced active area of the compensating diaphragm.

According to still another aspect of the invention, a breathing dispensing valve is provided comprising an admission pressure chamber with an inlet connected to a pressurized gas source, a back pressure chamber with a breathing gas outlet leading to a user and with a valve seat, a working diaphragm, a valve drive and safety and admission pressure compensation means. The working diaphragm is connected to the valve drive and is disposed between the admission pressure chamber and the back pressure chamber. The working diaphragm closes a connection between the admission pressure chamber and the back pressure chamber in a seated position on the valve seat and moves in response to forces acting on the working diaphragm including pressure acting on an admission pressure chamber side of the working diaphragm and pressure acting on a back pressure chamber side of the working diaphragm. The valve drive is associated with a push rod that connects to the working diaphragm. The valve drive acts on the working diaphragm in a drive state, to help lift the working diaphragm from the valve seat into an open position, opening the connection between the admission pressure chamber and not acting on the working diaphragm in a non-drive state to not help lift the working diaphragm from the valve seat. The safety and admission pressure compensation means is for providing a compensating force to counteract admission pressure chamber forces acting on the working diaphragm and for liming a maximum pressure of the admission pressure. The safety and admission pressure compensation means includes a compensation chamber connected to the admission pressure chamber, an expansion chamber having an expansion chamber pressure and a compensating diaphragm disposed between the compensation chamber and the expansion chamber and connected to the push rod. The compensating diaphragm has a variable active surface area that is acted on, on a compensation chamber side by admission pressure and acted on, on an expansion chamber side by expansion chamber pressure. The variable active surface changes to limit the force of admission pressure acting on the compensating diaphragm to limit the compensating force acting on the working diaphragm.

The safety and admission pressure compensation means advantageously comprises a support surface of the expansion chamber. The support surface extends at a spaced location from the compensating diaphragm. A deformation zone is defined by the compensating diaphragm. The deformation zone is brought into contact with the support surface in a deformation zone contact state, based on admission pressure. Expansion chamber pressure acts on the compensating diaphragm. The compensating diaphragm has a reduced surface exposed to admission pressure in the deformation zone contact state, liming the compensating force acting on the working diaphragm due to a reduced active area of the compensating diaphragm.

The advantage of the present invention is essentially that an elastic compensating diaphragm performing the admission pressure compensation is provided with a deformation zone, which is in contact with a support surface in case of a corresponding path of deformation and thus reduces the active area of the compensating diaphragm. The force that closes the dispensing valve thus becomes weaker and the maximum pressure that can be reached is limited in the area of the valve chambers, which are exposed to the admission pressure. The pressure in the area of these valve chambers can be set in this manner to a limit value up to which the working diaphragm lies sealingly on the corresponding valve crater. The limit value for the maximum pressure can be varied by varying the area of the deformation zone that is in contact with the support surface.

The compensating diaphragm is advantageously provided with a solid middle part connected to the push rod, and a flexible outer part, which can be deformed by admission of pressure and which is deformed by the admission pressure in the direction of the support surface, is located at the middle part. When the deformable outer part lies completely on the support surface, only the area of the middle part is decisive as an active area for the admission pressure compensation. The middle part consists for this purpose of a solid material, which cannot be deformed by the pressure.

It is especially advantageous to provide a circumferential bead, which is designed for good deformability, in the area of the outer part. The limit value for the pressure can be varied by varying the design embodiment of the bead and the thickness of the material of the deformable outer part in the area of the groove as well as the distance between the compensating diaphragm and the support surface.

An exemplary embodiment of the present invention is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
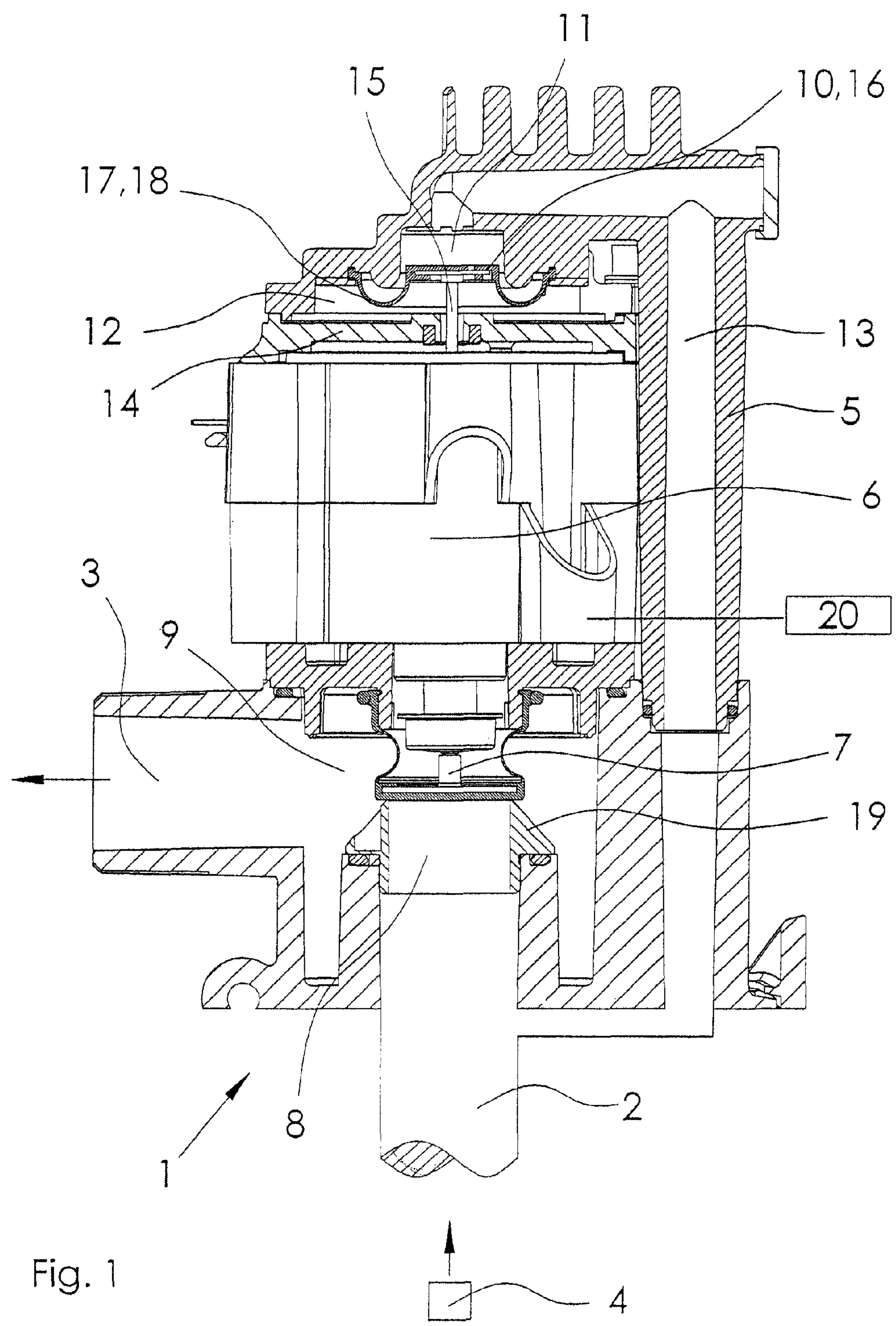
FIG. 1 is a longitudinal sectional view of a dispensing valve according to the invention.

Referring to the drawings in particular, FIG. 1 illustrates a dispensing valve 1 with admission pressure compensation with a gas inlet 2 for connection to a pressurized gas source 4 for breathing gas and with a gas outlet 3, which leads to a user, not shown more specifically. A magnetic drive 6, a working diaphragm 7 between an admission pressure chamber 8 and a back pressure chamber 9 and a compensating diaphragm 10 between a compensation chamber 11 and an expansion chamber 12 are arranged in a valve housing 5. The compensation chamber 11 is connected to the admission pressure chamber 8 via a pressure line 13. The expansion chamber 12 is at the pressure level of the ambient atmosphere and has a support surface 14, which is located opposite the compensating diaphragm 10 and extends in parallel to the compensating diaphragm 10. The compensating diaphragm 10 is connected to the working diaphragm 7 via a push rod 15 of the magnetic drive 6. The compensating diaphragm 10 has a solid middle part 16, which is directly connected to the push rod 15, and a flexible outer part 17 with a circumferential, flexible bead 18 as a deformation zone. The working diaphragm 7 lies on a valve crater 19. The surfaces of the working diaphragm 7 and of the compensating diaphragm 10, which are exposed to the admission pressure, are designed such that the working diaphragm 7 lies on the valve crater 19 and the gas flow from the gas inlet 2 to the gas outlet 3 is interrupted in the currentless state of the magnetic drive 6. The active area of the compensating diaphragm 10 is larger than the active area of the working diaphragm 7. If the magnetic drive 6 is actuated by a control source 20, the working diaphragm 7 is lifted off from the valve disk 19 and gas flows from the pressurized gas source 4 to the gas outlet 3. The opening force to be generated by the magnetic drive 6 arises from the area ratios of the working diaphragm 7 to the compensating diaphragm 10.

Figure 2:
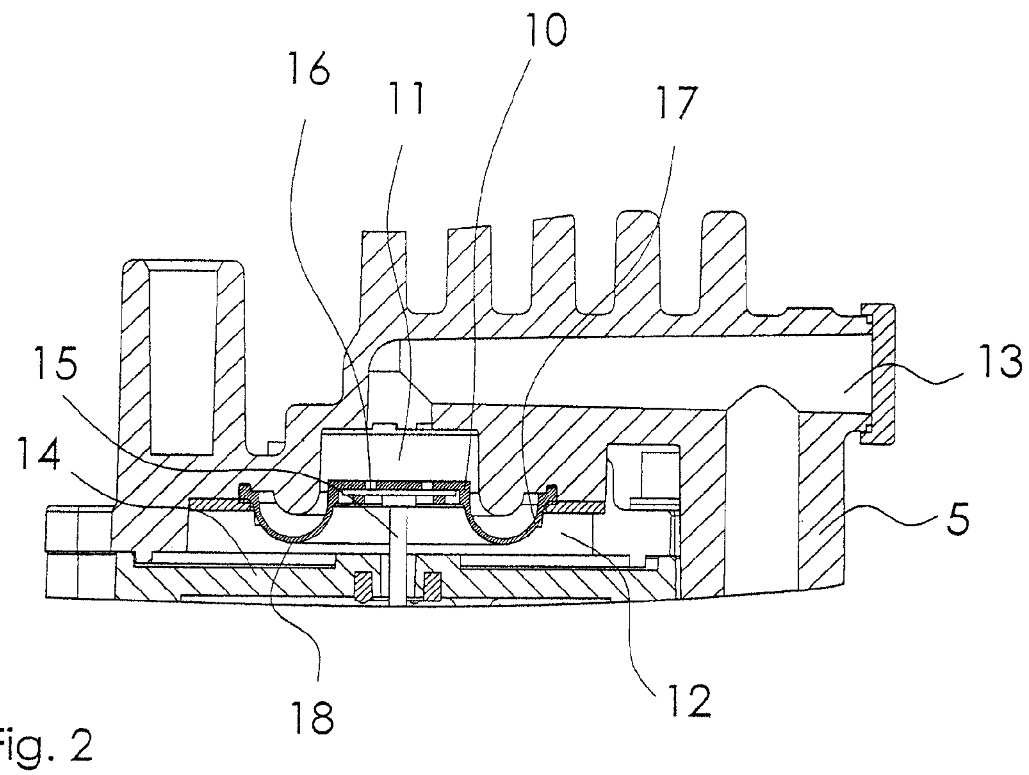
FIG. 2 is a detail view of the dispensing valve according to FIG. 1 in the area of the compensating diaphragm.

FIG. 2 illustrates a detail of the dispensing valve 1 in the area of the compensating diaphragm 10. Identical components are designated by the same reference numbers as in FIG. 1. The compensating diaphragm 10 is shown in FIG. 2 in a state in which a pressure below a predetermined pressure limit value is present within the compensation chamber 11.

Figure 3:
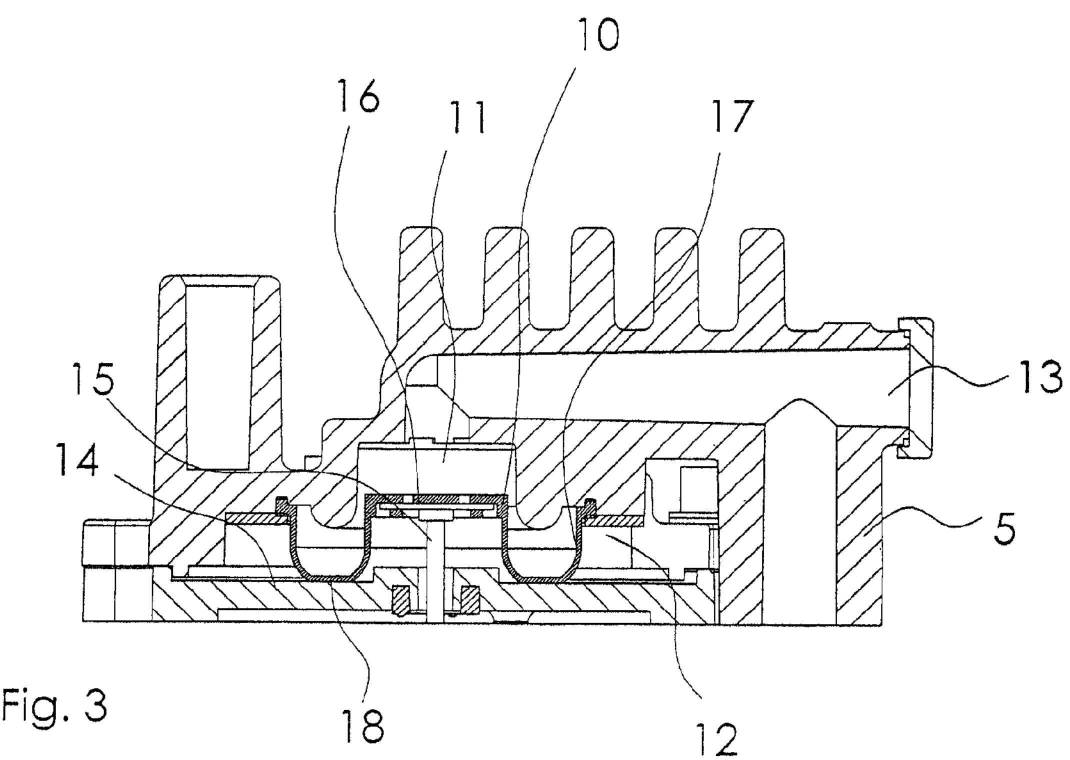
FIG. 3 is a detail view showing the dispensing valve according to FIG. 2 in the case the pressure exceeds a limit value.

FIG. 3 illustrates a detail of the dispensing valve 1 corresponding to FIG. 2 in the case in which the pressure within the compensation chamber 11 has exceeded the pressure limit value. The bead 18 within the flexible outer part 17 is deformed now to the extent that it is in contact in some sections with the support surface 14. Only the fixed middle part 16 is present as an active area exposed to the admission pressure. The compensating force acting on the working diaphragm 10 also decreases due to the reduced active area of the compensating diaphragm 10, as a result of which the working diaphragm 7 is lifted off from the valve crater 19. The pressure within the admission pressure chamber 8 is lowered as a result until the reduced force acting on the compensating diaphragm 10 is again sufficient to press the working diaphragm 7 against the valve seat 19. This leads to a pressure limitation for the areas of the admission pressure chamber 8, the pressure line 13 and the compensation chamber 11, which is fully exposed to the admission pressure.

While a specific embodiment of the invention have been shown and described in detail to illustrate the application of the principles of the invention, it will be understood that the invention may be embodied otherwise without departing from such principles.

What is claimed is:

1. A dispensing valve with admission pressure compensation, the dispensing valve comprising:

an admission pressure chamber;

a back pressure chamber;

a valve drive;

a working diaphragm between said admission pressure chamber and said back pressure chamber;

a compensation chamber connected to said admission pressure chamber;

an expansion chamber;

a compensating diaphragm between said compensation chamber and said expansion chamber, said expansion chamber having a support surface extending at a spaced location from said compensating diaphragm;

a push rod actuated by said valve drive and connecting said working diaphragm to said compensating diaphragm; and a deformation zone within said compensating diaphragm, said deformation zone being brought into contact with said support surface by admission pressure in said compensation chamber providing a reduction of an active area of said compensation diaphragm; a housing defining said admission pressure chamber, said back pressure chamber, said compensation chamber and said expansion chamber; a pressure line connecting said admission pressure chamber to said compensation chamber to communicate pressure from said admission pressure chamber to said compensation chamber; said push rod transmitting an actuating force between said valve drive, said working diaphragm and said compensating diaphragm relative to said housing.

2. A dispensing valve in accordance with claim 1, wherein said compensating diaphragm consists of a solid middle part connected to said push rod and a flexible outer part that is deformable by admitting pressure.

3. A dispensing valve in accordance with claim 2, wherein said outer part has a circumferential bead as a deformation zone.

4. A breathing dispensing valve with admission pressure compensation, the dispensing valve comprising:

an admission pressure chamber with an inlet connected to a pressurized gas source;

a back pressure chamber with a breathing gas outlet leading to a user and with a valve seat;

a valve drive;

a working diaphragm connected to said valve drive and disposed between said admission pressure chamber and said back pressure chamber, said working diaphragm closing a connection between said admission pressure chamber and said back pressure chamber in a seated position on said valve seat, said valve drive assisting a movement of said working diaphragm from said seated position into an open position opening the connection between said admission pressure chamber and said back pressure chamber;

a compensation chamber connected to said admission pressure chamber;

an expansion chamber having an expansion chamber pressure;

a compensating diaphragm disposed between said compensation chamber and said expansion chamber and being acted on, on a compensation chamber side by admission pressure and being acted on, on an expansion chamber side by expansion chamber pressure, said expansion chamber having a support surface extending at a spaced location from said compensating diaphragm;

a push rod connected to said valve drive and connecting said working diaphragm to said compensating diaphragm; and a deformation zone defined by said compensating diaphragm, said deformation zone being brought into contact with said support surface in a deformation zone contact state, based on admission pressure and expansion chamber pressure acting on said compensating diaphragm, said compensating diaphragm having a reduced surface exposed to admission pressure in said deformation zone contact state, limiting a compensating force acting on the working diaphragm due to a reduced active area of said compensation diaphragm; a housing defining said admission pressure chamber, said back pressure chamber, said compensation chamber and said expansion chamber; a pressure line connecting said admission pressure chamber to said compensation chamber to communicate pressure from said admission pressure chamber to said compensation chamber; said push rod transmitting an actuating force between said valve drive, said working diaphragm and said compensating diaphragm relative to said housing.

5. A dispensing valve in accordance with claim 4, wherein said compensating diaphragm consists of a solid middle part connected to said push rod and a flexible outer part that is deformable by admitting pressure.

6. A dispensing valve in accordance with claim 5, wherein said outer part has a circumferential bead as a deformation zone.

7. A dispensing valve in accordance with claim 4, wherein said expansion chamber pressure is ambient pressure.

8. A breathing dispensing valve comprising:

an admission pressure chamber with an inlet connected to a pressurized gas source;

a back pressure chamber with a breathing gas outlet leading to a user and with a valve seat;

a working diaphragm connected to said valve drive and disposed between said admission pressure chamber and said back pressure chamber, said working diaphragm closing a connection between said admission pressure chamber and said back pressure chamber in a seated position on said valve seat and moving in response to forces acting on said working diaphragm including pressure acting on an admission pressure chamber side of said working diaphragm and pressure acting on a back pressure chamber side of said working diaphragm;

a valve drive with a push rod connected to said working diaphragm, said valve drive acting on said working diaphragm in a drive state, to help lift said working diaphragm from said valve seat into an open position, opening the connection between said admission pressure chamber and said back pressure chamber and not acting on said working diaphragm in a non-drive state to not lift said working diaphragm from said valve seat;

a safety and admission pressure compensation means for providing a compensating force to counteract admission pressure chamber forces acting on said working diaphragm and for limiting a maximum pressure of the admission pressure, said safety and admission pressure compensation means including a compensation chamber connected to said admission pressure chamber, an expansion chamber having an expansion chamber pressure and a compensating diaphragm disposed between said compensation chamber and said expansion chamber and connected to said push rod, said compensating diaphragm having a variable active surface area that is acted on, on a compensation chamber side by admission pressure and acted on, on an expansion chamber side by expansion chamber pressure, said variable active surface changing to limit the force of admission pressure acting on said compensating diaphragm to limit the compensating force acting on the working diaphragm, said safety and admission pressure compensation means including a support surface of said expansion chamber, said support surface extending at a spaced location from said compensating diaphragm, and a deformation zone defined by said compensating diaphragm, said deformation zone being brought into contact with said support surface in a deformation zone contact state, based on admission pressure and expansion chamber pressure acting on said compensating diaphragm, said compensating diaphragm having a reduced surface exposed to admission pressure in said deformation zone contact state, limiting the compensating force acting on the working diaphragm due to a reduced active area of the compensating diaphragm; a housing defining said admission pressure chamber, said back pressure chamber, said compensation chamber and said expansion chamber; a pressure line connecting said admission pressure chamber to said compensation chamber to communicate pressure from said admission pressure chamber to said compensation chamber; said push rod transmitting an actuating force between said valve drive, said working diaphragm and said compensating diaphragm relative to said housing.

9. A dispensing valve in accordance with claim 8, wherein said compensating diaphragm consists of a solid middle part connected to said push rod and a flexible outer part that is deformable by admitting pressure.

10. A dispensing valve in accordance with claim 9, wherein said outer part has a circumferential bead as a deformation zone.

11. A dispensing valve in accordance with claim 8, wherein said expansion chamber pressure is ambient pressure.

* * * * *